United States Patent [19]

Snow

[11] Patent Number: 5,477,716
[45] Date of Patent: Dec. 26, 1995

[54] APPARATUS FOR MONITORING MOISTURE IN A GAS STREAM

[75] Inventor: James T. Snow, Nashua, N.H.

[73] Assignee: Millipore Corporation, Bedford, Mass.

[21] Appl. No.: 281,286

[22] Filed: Jul. 27, 1994

Related U.S. Application Data

[63] Continuation-in-part of Ser. No. 958,384, Oct. 8, 1992, Pat. No. 5,339,675.

[51] Int. Cl.⁶ .......................... B01J 29/00; G01N 31/06
[52] U.S. Cl. .......................... 73/24.01; 73/31.06; 436/40
[58] Field of Search ...................... 73/24.01, 24.04, 73/24.06, 24.03, 31.06

[56] References Cited

U.S. PATENT DOCUMENTS

| | | | |
|---|---|---|---|
| 3,164,004 | 1/1965 | King, Jr. | 73/24.06 |
| 4,111,036 | 9/1978 | Frechette et al. | 73/23 |
| 5,189,902 | 3/1993 | Groeninger | 73/24.06 |
| 5,212,988 | 5/1993 | White et al. | 73/599 |
| 5,339,675 | 8/1994 | DiLeo et al. | 73/24.04 |
| 5,364,797 | 11/1994 | Olsen et al. | 436/501 |

*Primary Examiner*—Hezron E. Williams
*Assistant Examiner*—J. David Wiggins
*Attorney, Agent, or Firm*—Andrew T. Karnakis; Paul J. Cook

[57] ABSTRACT

A device is provided comprising a piezoelectric material and at least one non-crystalline non-crystalline metal oxide, crystalline-non-zeolite metal oxide and mixtures thereof coating chemically reactive with trace quantities of water in chemically reactive and inert gases. The piezoelectric material is bonded to a conductor for delivering an alternating electric current and to a conductor for transmitting resonant vibration frequency of the crystal. The reactive metal oxide coating has an effective thickness which provides a serviceable life for the coating while not being so thick as to prevent vibration of the piezoelectric material.

14 Claims, 2 Drawing Sheets

APPARATUS FOR MONITORING MOISTURE IN A GAS STREAM

REFERENCE TO RELATED APPLICATION

This application is a continuation-in-part of U.S. application Ser. No. 07/958,384, filed Oct. 8, 1992, which has become U.S. Pat. No. 5,339,675 as of Aug. 23, 1994.

BACKGROUND OF THE INVENTION

This invention relates to a method and apparatus for detecting water impurity in a gas stream. More particularly, this invention relates to a method and apparatus for detecting water impurity utilizing a piezoelectric crystal coated with a metal oxide reactive with water.

At the present time ultrapure gas streams are utilized in chemical reactions such as in the semiconductor industry. These chemical reactions usually are conducted in sealed containers to maintain purity since the gases often times are toxic and are conducted under low pressure in order to decrease the probability of unwanted side reactions. In order to maintain the requisite gas purity, the gas is treated, prior to entering the reaction chamber, in order to remove impurities therefrom. It is general practice to pass the gas through a bed of resin particles which are interactive with impurities such as water in the gas. Over time, the capacity of the bed of resin particles for interacting with the impurities is depleted to a point where breakthrough of impurities from the resin bed occurs and the impurities enter the reaction zone it is difficult to predict when undesirable depletion of resin capacity occurs so that in the absence of independent monitoring means, premature or late removal of the resin is likely. Premature resin removal results in increased resin cost while late removal results in expensive damage to reaction product. It is additionally desirable to have a means for continuously monitoring the gas purity level and providing a measure of gas impurity concentration.

It has been proposed in U.S. Pat. No. 5,138,867 to provide a detection system for sensing concentration of impurities in a gas stream which includes a sensing device which can be hygrometric, spectrophotometric, piezoelectric or colorimetric. The specific piezoelectric device disclosed is a surface acoustical wave (SAW) device. In a SAW device, an acoustical wave is passed along a surface coating on a substrate to measure the change in mass at the interface between the coating and the substrate. Mass change in the coating is caused by reaction of the coating with impurities in a gas which contacts the coating. Accordingly, a reactive polymer coating material is described that is consumed over time and regenerable. In the SAW device, the coating must be thin; on the order of a wavelength of the acoustic wave or thinner in order to permit accurate measurement of impurity concentration. While this device is extremely sensitive to impurity concentration change, i.e. in the picogram level, it is too sensitive for use in a device requiring an extended service, i.e., about one year or more, since the thickness of the coating necessary to have the capacity for extended lifetimes quickly exceeds that which permits accurate measurements. The detection of water vapor using materials like silica gel and alumina on piezoelectric materials was proposed in U.S. Pat. No. 3,385,100. These types of metal oxide coatings absorb moisture through a physisorption, rather than chemisorption, mechanism. Water adsorption on these types of coatings occur principally through dipole bonds (H-bonding) with surface hydroxyls. The approximate water vapor pressure at 25° C. for absorbants like alumina are shown in the table below (Shriver, D. F.; Drezdzon, M. A. "The Manipulation of Air-Sensitive Compounds", 2nd.ed.; John Wiley & Sons, Inc.: New York. 1986; p 72):

| Material | Water Vapor Pressure (torr) |
|---|---|
| Molecular Sieves | $1 \times 10^{-3}$ |
| Alumina (active) | $1 \times 10^{-3}$ |
| Silica gel | $2 \times 10^{-3}$ |

Absorbants such as alumina, silica gel and molecular sieves exhibit a steady increase in the water vapor pressure as more moisture is absorbed. This continual increase is undesirable, since the sensitivity for moisture steadily decreases as more moisture is absorbed. In addition, due to the reversible adsorption-desorption of moisture from these type of coatings, the coated crystal would need to be located within a carefully temperature controlled environment to eliminate any temperature effects on the physisorption.

A scavenger for oxygen and water vapor impurities comprising metal hydrides are disclosed in U.S. Pat. Nos. 4,950,419 and 4,716,181. However, these devices are not useful for selective reaction with water in an oxygen gas containing stream since coatings of the device are reactive with both oxygen and water.

It would be desirable to provide a means for detecting water vapor in a gas stream which is useful and accurate for extended times. In addition it would be desirable to provide such a means for detecting water vapor capable of quantifying impurity concentration in a gas, particularly a gas stream consisting of or containing oxygen gas.

SUMMARY OF THE INVENTION

The present invention provides a coated piezoelectric apparatus for detecting the presence of water impurity in a wide variety of gases. A piezoelectric crystal is coated on one or more opposing surfaces with a non-crystalline metal oxide which reacts with water to form a metal hydroxide. The metal oxide can be deposited on the piezoelectric crystal by a suitable thin film deposition process. Alternatively the metal oxide coating can be formed in situ by first coating the crystal with a metal which is reactive with oxygen followed by exposure to an oxygen-containing gas to convert the metal coating to the desired metal oxide. The mass of reactive metal oxide coating applied is large enough so that there is enough material to continue to react with water for the service lifetime that is desired, while not being so heavy as to prevent or substantially reduce vibration of the piezoelectric crystal due to its mass or the mass of the reaction product. The crystal is subjected to an alternating electric field and the resonant vibration caused by the electric field is detected. The reaction of water with the reactive metal oxide coating will form a metal hydroxide with an accompanying change of mass. The mass change will cause a change in resonant frequency, i.e., a mass increase causes a resonant frequency decrease due to a damping effect which is measured. The resonant frequency measured can be correlated to water impurity concentration in the incoming gas by means of a standard curve. The piezoelectric crystal can be coated with a protective polymer such as poly(vinylidene fluoride) (PVDF) or polytetrafluoroethylene to protect the piezoelectric from corrosive gases such as hydrogen fluoride. The reactive coating is coated on the protective polymer. The combined mass of the two coatings must meet the mass criteria set forth above.

DESCRIPTION OF SPECIFIC EMBODIMENTS

Figure 4:
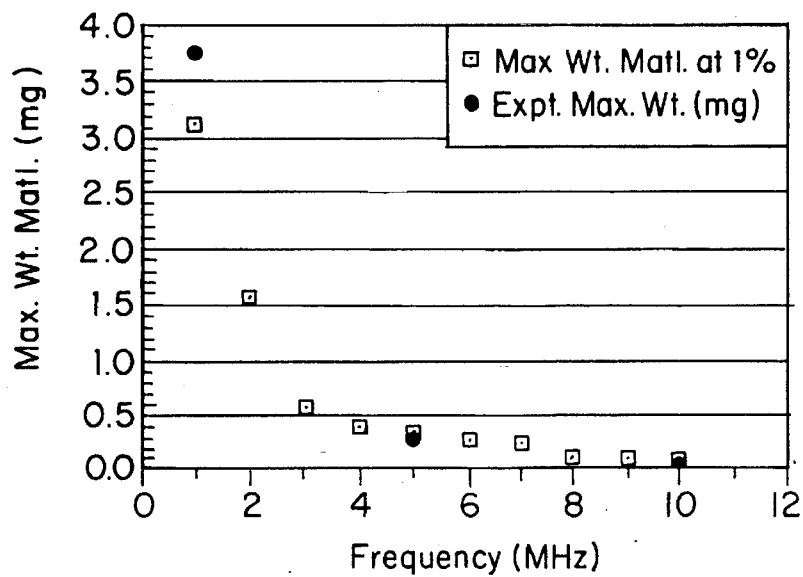
FIG. 4 is a graph showing the maximum weight of material that can be deposited on a crystal and remain within the crystal linear range.

The coated piezoelectric crystals of this invention comprise a piezoelectric substrate such as natural quartz, lithium niobate, lead metaniobate, lead zirconate titanate, poly(vinylidene difluoride) (PVDF), Rochelle salts, tourmaline, ethylenediamine tartrate, dipotassium tartrate, ammonium dihydrogen phosphate or the like, preferably quartz (and PVDF in hydrogen fluoride gas streams). The coating is applied to one or both of the largest surfaces of the substrate. The behavior of the piezoelectric crystals can be explained using the Sauerbrey equation:

$$\Delta f = -f_o^2 m/NA\rho$$

wherein $\Delta f$ is the observed frequency change, $f_o$ is the fundamental frequency of the crystal, m is the mass change at the electrode surface, N is the frequency constant for the crystal, A is the surface area of the deposit, and $\rho$ is the density of the piezoelectric crystal. As evidenced by the equation, the observed frequency change is linearly dependent on the mass change but varies to the square of the fundamental frequency. Thus, a 2.0-MHz crystal will be four times more sensitive than a 1.0 MHz crystal. Good correlation has been found between the observed and calculated frequency change when the crystal linear range is assumed to be 1% of $f_o$ as shown in FIG. 4. Outside this range, this linear relationship between frequency and mass change will deteriorate and above a critical mass, the crystal will cease to oscillate. Thus, as shown in FIG. 4, the maximum amount of material that the crystal can accommodate and still vibrate within the linear response range will vary according to the frequency of the piezoelectric crystals utilized and is generally between about 0.1 and 3.5 milligrams.

Suitable metal oxide coatings are those which react with water, permit detection of water at concentrations of 1 part per billion (ppb) and do not add contaminant to purified gas. The non-crystalline metal oxide coatings most useful in the present invention are those which react with water to form the metal hydroxide which then reacts further with water to form hydrates of the hydroxide. Metal oxides which merely adsorb or absorb water are not useful in the present invention. The metal should be reactive with water at a temperature between about 10° and 60° C., preferably between about 20° and 35° C. to form a metal hydroxide product having a melting point of at least about 60° C. Representative suitable metal oxides include the oxides of Groups IA and IIA elements, i.e. lithium, magnesium, potassium, strontium, barium, sodium, calcium or the like. It is preferred to utilize the metal oxides formed of a metal having a low molecular weight such as lithium or magnesium since the mass change as a result of reaction with water is larger and more easily detectable as compared to coatings containing higher molecular weight metals. The chemical reaction of the desired metal oxides of this invention differs significantly from the physical interaction of the metal oxides e.g. alumina, silica gel and molecular sieves with moisture. The water vapor absorption isotherms for the desired metal oxides have plateau regions corresponding to the different phases and do not continuously increase as observed with silica gel and alumina. Therefore, the reactivity and sensitivity toward moisture is constant in these regions. This extends the capability of these coatings for accurate low-level moisture detection and simplifies the interpretation of moisture calibration curves. In addition, the chemical reaction of moisture with the desired metal oxides eliminates the need for careful temperature control that is required with the other metal oxide coatings that have adsorption-desorption equilibria. One of the desired coatings, barium oxide, additionally has a lower water vapor pressure of $7 \times 10^{-4}$ torr compared to alumina and related metal oxides. In addition, analysis of reaction kinetic data showed similar reaction probabilities for the reactions of water with BaO and Ba metal, a known getter for moisture (Verhoeven, J.; Van Doveren, H. *Applications of Surface Science* 1980, 6, 225)

The detector of this invention is useful in monitoring water vapor impurity concentration in oxygen containing gases such as oxygen or nitrous oxide; inert gases, such as helium, argon, nitrogen; silicon containing gases such as silane, dichlorosilane, trichlorosilane; dopants such as arsine, phosphine, diborane; etchants such as halocarbon 14, halocarbon 16, halocarbon 218, sulfur hexafluoride, chlorine, hydrogen bromide or reactants such as hydrogen chloride, hydrogen fluoride or ammonia. When monitoring an oxygen-containing gas, a metal coating is first converted to a metal oxide by the gas stream which then is reactive with water vapor to produce the effects discussed above. The mass change corresponding to this conversion must not exceed the maximum mass specified for the crystal discussed above. Alternatively, the metal oxide may be deposited on the piezoelectric crystal by a suitable thin film deposition technique.

Figure 1:
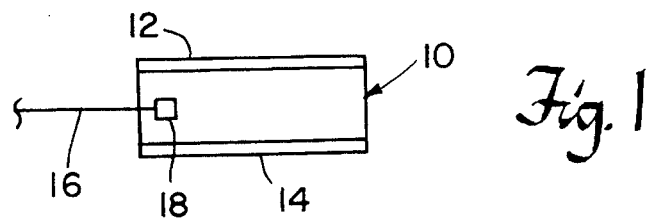
FIG. 1 is a side view of a coated piezoelectric crystal device of this invention.

Referring to FIG. 1, the composite structure of this invention includes a piezoelectric crystal which is coated with the metal oxide coating materials of this invention set forth above to form coatings 12 and 14. A conductive lead wire 16 such as a copper wire is bonded to crystal 10 such as with solder 18 in order to input alternating electrical energy into crystal 10.

Figure 2:
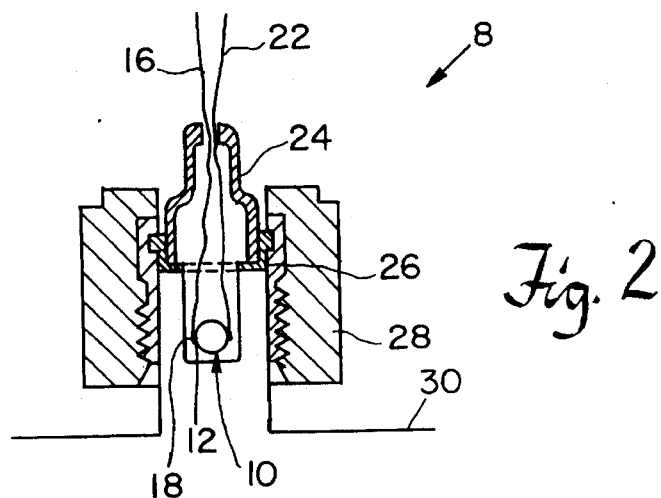
FIG. 2 is a top view of an apparatus of this invention.

Referring to FIG. 2, an apparatus of this invention is shown including the piezoelectric crystal coating 12 and connected to lead wire 16. A second lead wire 22 is bonded to piezoelectric crystal 10 which transmits vibration of the coated crystal to an electronic circuit such as described below. The electronic circuit monitors the frequency of vibration of the energized crystal. The coatings 12 and 14 are applied by an acceptable thin film deposition technique, e.g., sputtering. The film can be applied as the metal oxide directly or as the metal which then can be converted to the metal oxide by reaction with oxygen. For the deposition of a metal conductor e.g. magnesium, DC sputtering is a possible mode. For other metals or metal oxides, e.g. barium, barium oxide, RF is the recommended sputtering technique. In a process of utilizing an RF planar magnetron sputtering system for the deposition of barium, e.g., Model CrC-100 Planar Magnetron Sputtering System with optional 200 watt RF power supply manufactured by Plasma Sciences, Inc., a potential is applied to a barium target. In the sputtering process, the barium target will become negatively self-biased creating an enrichment of ions in front of the target. The ions strike the target and sputtering is obtained. The crystal is positioned on a pedestal located at a distance of one to three inches from the bottom of the sputtering head. The crystal is masked so deposition occurs only on the desired areas of the piezoelectric electrodes. Typical sputtering operations with this piece of equipment are performed at a pressure range of 2 to 10 mtorr and RF power of 50 to 150 W with argon as the sputtering gas. For the sputter deposition of metal oxides, reactive RF sputtering may be employed with 1–5% oxygen in argon as the sputtering gas.

The oscillator design is based on a CMOS Pierce Oscillator. The basic physics internal to the crystal is that of a sound wave propagating through the crystal. The initial electrical input at one voltage difference causes an expansion of the crystal. The initial voltage is produced by one end of the inverter gate due to its 180° phase difference from the other end of the inverter. The piezoelectric crystal behaves electrically like a high Q(quality) LC network, or physically like a mass spring. As the mass per unit length of the spring changes, so will the frequency of the springs oscillations. By changing the mass on the surface of the crystal frequency changes of the crystal oscillator can be detected.

Two CMOS Pierce Oscillators are used in the electronics circuit. One oscillator is used as a reference, the other as a mass sensor. The two signals are fed into a flip-flop that gives the difference frequency of the two crystals. This serves two purposes; one to null Out any temperature effects, the other to give a smaller frequency value, e.g., 1,000,000 Hz reference signal, and 999,000 Hz sensor signal, will produce a 1,000 Hz difference frequency. The difference frequency is applied to a microcontroller counter input and frequency cycles summed for a given time period. Knowing the number of total cycles and the time period, frequency in Hz can be calculated. A ten second sample time gives 1/10 Hz resolution of the difference frequency.

Figure 3:
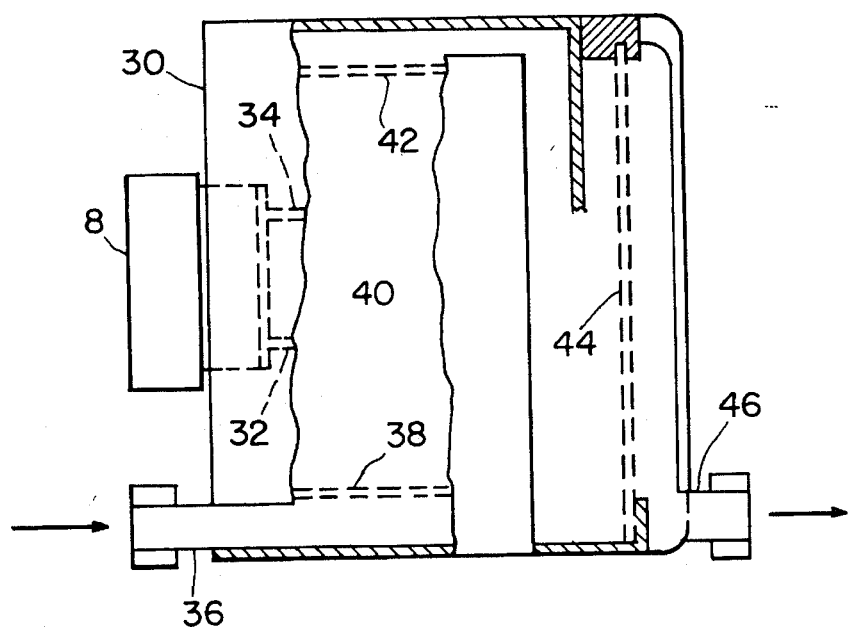
FIG. 3 is a schematic view illustrating the use of the apparatus of this invention.

Referring to FIG. 3, the sensor apparatus 8 of this invention is positioned on housing 30 and includes a gas inlet 32 and a gas outlet 34. Gas to be purified is introduced through inlet 36, through screen 38 and into resin bed 40. Optional resin bed 40 functions to scavenge water vapor from the incoming gas. Purified gas is passed out screen 42, through final filter 44 and through outlet 46 to a zone for chemical reaction (not shown). Alternate device configurations are possible, including a device in which the coated crystal is mounted directly within the flowing gas stream.

The following example illustrates the present invention and is not intended to limit the same.

EXAMPLE 1

Figure 5:
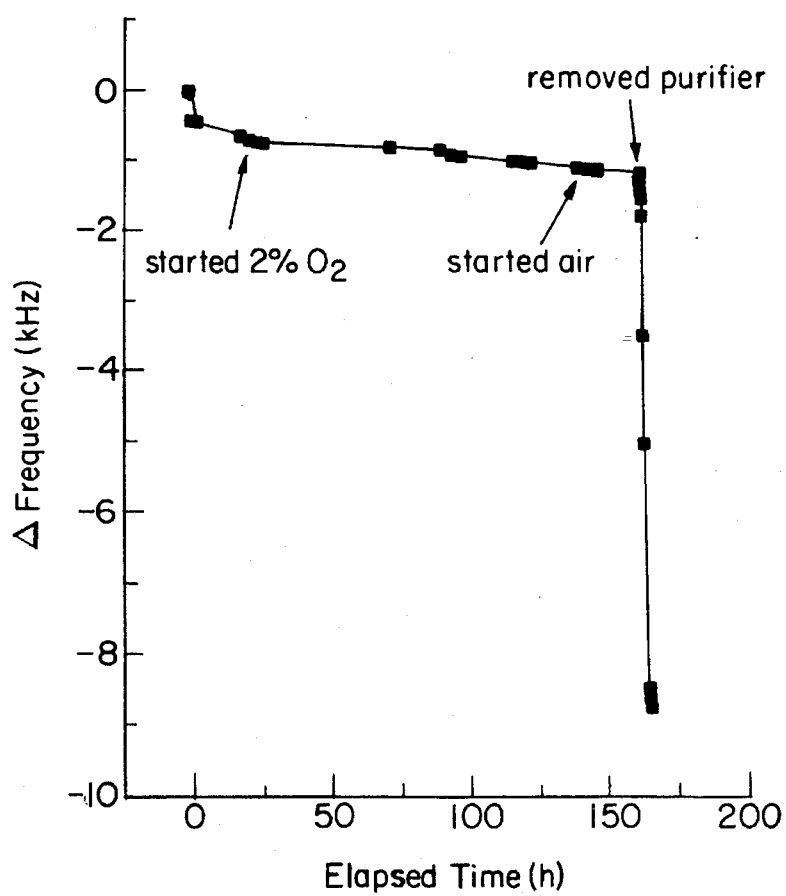
FIG. 5 shows the effect of pressurized air contact with the coated piezoelectric crystal device of this invention.

A stainless steel housing consisting of all stainless steel components, metal-to-metal face seal and metal gasket seal connections and inlet and outlet diaphragm valves to seal the housing from outside atmosphere when required was constructed to permit testing of coated piezoelectric quartz crystals. A quartz crystal with fundamental frequency of 5.050 MHz was RF sputter coated in an argon glove box with barium metal at 55 W, 5 mTorr pressure for 7 minutes each side to deposit a total of 166 µg of barium metal and decreased the frequency of the crystal to 5.014 MHz. The crystal, previously mounted on a HC-51/U type holder with glass feedthroughs and holder welded onto metal header, was inserted into the stainless steel housing and sealed with metal gasket seal. The housing was removed from the glove box and connected to a high purity test stand. Connected to the upstream diaphragm valve of the housing was a Wafer-pure® Mini XL gas purifier (Model No. WPMV200SC) to remove water vapor from the test gas. A flow of purified nitrogen from a cryogenic source at 1.0 slpm was started through the housing containing the barium-coated crystal. After ca. 20 hours, the gas was switched to a 2% oxygen in argon mixture to accelerate the conversion of the barium coating to barium oxide. The gas flow was periodically stopped to pressurize the housing with the oxygen gas mixture, especially during overnight periods. After ca. 143 hours, the gas was switched to air (Grade 0.1, [$H_2O$]<3 ppm) to convert any remaining accessible barium to barium oxide. The purifier was removed after 162 hours to challenge the formed barium oxide coated sensor to the unpurified air. As shown in FIG. 5, exposure of the sensor to moisture resulted in a large and immediate frequency decrease corresponding to conversion of the sensor coating to barium hydroxide.

I claim:

1. A sensing device for measuring water content in a stream of purified gases which comprises:

a piezoelectric material having an effective mass of a non-crystalline metal oxide coating on at least one surface of said sensing device, with said coating formed of a composition chemically reactive with water to form a metal hydroxide product, said coating having a mass which permits said material to vibrate in response to applied alternating electrical current, means for applying an alternating electrical current to said piezoelectric material and means for measuring frequency of vibration of said piezoelectric material.

2. The device of claim 1 wherein said material has said coating on two opposing surfaces.

3. The device of claim 1 wherein said piezoelectric material is quartz.

4. The device of claim 2 wherein said piezoelectric material is quartz.

5. The device of claim 1 wherein said coating is barium oxide.

6. The device of claim 2 wherein said coating is barium oxide.

7. The device of claim 3 wherein said coating is barium oxide.

8. The device of claim 4 wherein said coating is barium oxide.

9. The device of claim 1 wherein said piezoelectric material is poly(vinylidene fluoride).

10. The device of claim 2 wherein said piezoelectric material is poly (vinylidene fluoride).

11. The device of claim 1 wherein said coating includes a layer of protective material between said metal oxide coating and said piezoelectric material comprising poly(vinylidene fluoride).

12. The device of claim I wherein said coating includes a layer of protective material between said metal oxide coating and said piezoelectric material comprising polytetrafluoroethylene.

13. The device of claim 2 wherein said coating includes a layer of protective material between said metal oxide coating and said piezoelectric material comprising poly(vinylidene fluoride).

14. The device of claim 2 wherein said coating includes a layer of protective material between said metal oxide coating and said piezoelectric material comprising polytetrafluoroethylene.

* * * * *